United States Patent [19]

Ishikawa

[11] Patent Number: 5,236,830

[45] Date of Patent: Aug. 17, 1993

[54] METHOD OF ASSAY FOR ANTIGEN

[76] Inventor: Eiji Ishikawa, 24-1, Ohtsukadainishi 3-chome, Miyazaki-shi, Miyazaki, Japan

[21] Appl. No.: 431,476

[22] Filed: Nov. 3, 1989

[30] Foreign Application Priority Data

Nov. 10, 1988 [JP] Japan .................. 63-284925

[51] Int. Cl.⁵ .................. G01N 33/545; G01N 33/563
[52] U.S. Cl. .................. 435/7.5; 435/7.94; 436/512; 436/518; 436/527; 436/531; 436/822
[58] Field of Search .................. 435/79, 7.94, 7.95, 435/7.5, 961; 436/518, 531, 536, 543, 544, 546, 512, 527, 822

[56] References Cited

U.S. PATENT DOCUMENTS 4,020,151 4/1977 Bolz .................. 424/1.5

FOREIGN PATENT DOCUMENTS 0196787 10/1986 European Pat. Off. .
8600394 3/1987 PCT Int'l Appl. .

*Primary Examiner*—Mary E. Ceperley
*Attorney, Agent, or Firm*—Jacobson, Price, Holman & Stern

[57] ABSTRACT

A method of assay for antigen comprising the following sequential steps (A), (B), (C) and (D):

(A): the antigen to be assayed in a subject solution is bound with a functional group or marker to form a modified antigen;

(B): the modified antigen is bound to a carrier via an antibody against the antigen, and then the carrier is separated from the subject solution;

(C): Either (a) or (b):
  (a) the modified antigen is dissociated from the carrier; or
  (b) the modified antigen-antibody complex comprising the modified antigen and the antibody against the antigen is dissociated from the carrier; and (D): the modified antigen or modified antigen-antibody complex of Step (C) is assayed.

This method permits assay for antigens with high sensitivity based on characteristic features of the sandwich method, using an antibody against a single epitopic site, and also permits assay for low molecular substances, which have never been assayed by the conventional sandwich method, with higher sensitivity in comparison with the conventional competitive method.

7 Claims, 4 Drawing Sheets

METHOD OF ASSAY FOR ANTIGEN

BACKGROUND OF THE INVENTION

The present invention relates to a method of assay for antigen, specifically to a method of assay for antigen which permits assay for low molecular antigens (including haptens) with high sensitivity.

Assay of antigen in biocomponents, particularly those in human body fluids, is very important in clinical situations. It is widely used for endocrinologic examinations by hormone measurement, cancer diagnosis, quantitative determination of drugs and other purposes.

Microdetermination for antigens as mentioned above has conventionally been achieved by immunoassay methods, such as RIA, EIA and FIA.

The immunoassay methods can be roughly classified into two groups, one based on the competitive method and the other based on the sandwich method.

Immunoassay was first established as RIA based on the competitive method by Yallow et al. The competitive method is an assay method utilizing the inhibition of the binding of labeled antigen to antibody by the antigen to be assayed. When the amounts of the labeled antigen and antibody added are increased, the inhibition by a small amount of antigen to be assayed becomes undetectable. When the amounts of added labeled antigen and antibody are reduced, the ratio of labeled antigen bound to the antibody decreases, thus posing a limitation. Therefore, the detection limit is normally about 1 fmol ($10^{-15}$ mol)

On the other hand, the sandwich method is an assay method in which the antigen to be assayed is bound with both an antibody-coated carrier and a labeled antibody in a sandwich state. In this method, the detection limit is 100 to 1000 times superior to that of the competitive method, thus permitting assay at the amol ($10^{-18}$ mol) level. It has recently become common to assay protein hormones, such as TSH and hCG, by sandwich methods known as ELISA and IRMA.

However, there are some limitations posed on the sandwich methods as to measurable antigens. Specifically, the antigen to be assayed by the sandwich method needs to have at least two epitopic sites at a time at which the antigen can bind to the antibody, and low molecular antigens cannot be assayed by the sandwich method.

Also, even when the antigen is theoretically measurable by the sandwich method, it is difficult to obtain two antibodies against the two epitopic sites in some cases; in others, even when two antibodies against the two epitopic sites can be obtained, high titer antibody might be obtained at only one epitopic site, which hampers high sensitivity assay.

The object of the present invention is to provide a method of assay for antigen with high sensitivity based on characteristic features of the sandwich method, using only one antibody against a single epitopic site, specifically a method which permits assay for low molecular antigens (haptens), such as peptides, steroids and drugs, which have never been assayed by the conventional sandwich method, with sensitivity as high as that of the sandwich method.

SUMMARY OF THE INVENTION

The present inventor has found that the use of an antigen preliminarily modified by a functional group or marker makes it possible to directly assay the antigen in the subject solution as by the conventional sandwich method using an antibody against a single epitopic site, and that even when the antigen has only one epitopic site, it is possible to determine the antigen with much higher sensitivity than that of the competitive method, which culminated in the completion of the invention.

Accordingly, the present invention is a method of assay for antigen comprising the following steps (A), (B), (C) and (D), to be conducted in this order:

(A): the antigen to be assayed in the subject solution is directly bound with a functional group or a marker via a chemical bond to form a modified antigen.

(B): the modified antigen is bound to a carrier via an antibody against the antigen and then the carrier is separated from the subject solution (C): either (a) or (b):
 (a) the modified antigen is dissociated from the carrier.
 (b) the modified antigen-antibody complex comprising the modified antigen and the antibody against the antigen is dissociated from the carrier.

(D): the modified antigen or modified antigen-antibody complex of (C) is assayed.

Figure 1:
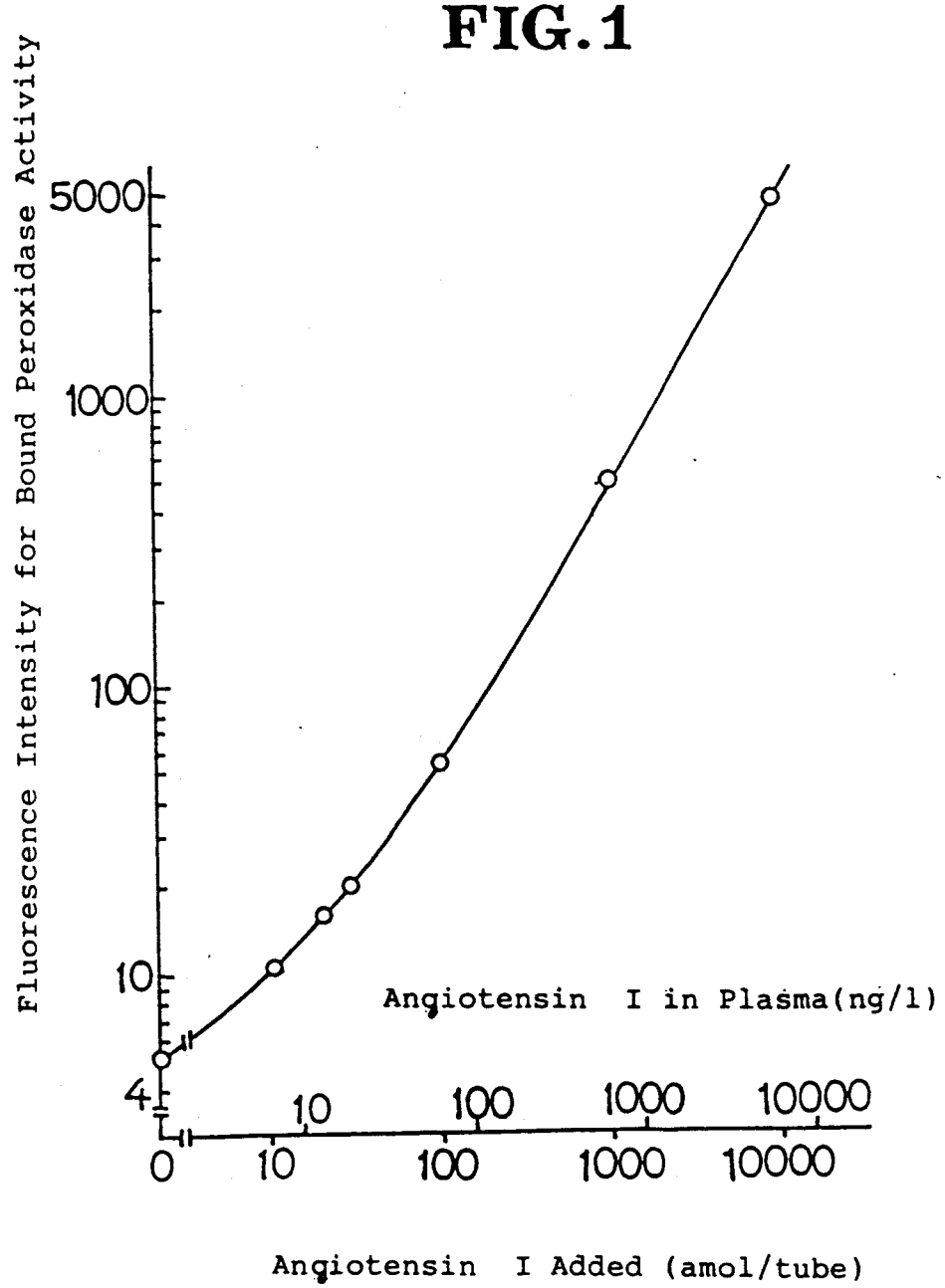
FIGS. 1, 2 and 4 show the standard curves of assay for antigen by the method of the present invention as obtained in Examples.

The present invention is hereinafter described in the order of step arrangement.

STEP (A)

A step to obtain a modified antigen in the subject solution.

Examples of the subject solution include body fluids, such as serum, plasma, cerebrospinal fluid, saliva and urine, and buffer solutions containing the antigen to be assayed. All substances having an epitopic site, or substantially all antigens measurable by conventional immunoassay methods can be assayed.

Examples of the antigen to be assayed include proteinous hormones, such as thyroid stimulating hormone (TSH) and human chorionic gonadotrophin (hCG); plasma proteins, such as fibrin degradation products (FDP) and C-reactive protein (CRP); carcinoembryonic protein, such as $\alpha$-fetoprotein (AFP) and carcinoembryonic antigen (CEA); and haptens, such as angiotensin I, vasopressin, somatostatin, atrial natriuretic hormone, endoserine, luteinizing hormone releasing hormone (LH-RH), kassinin and other peptides, progesterone, testosterone, cortisol and other steroids, total thyroxine ($T_4$), triiodothyronine ($T_3$), catecholamine and digoxin. Antigens categorized as haptens are desirable for the present invention. Particularly desirable antigens are peptides having an amino group in their molecular structure.

Any functional group can be used, as long as a substance which specifically binds with the functional group exists and the subject solution contains substantially no functional group or substance which specifically binds with the functional group. Examples of such functional groups include haptens, such as dinitrophenyl group, trinitrophenyl group and fluorescein group, and biotinyl.

Any marker can be used, as long as it can serve for immunoassay. Examples of such markers include enzymes, radioactive substances, luminescent substances, fluorescent substances and metal compounds.

Examples of usable enzymes include peroxidase, $\beta$-D-galactosidase and alkali phosphatase. Examples of usable radioactive substances include iodine and hydrogen. Examples of usable fluorescent substances include fluorescein isothiocyanate. Examples of usable luminescent substances include acridinium salts.

For the use as the marker to be bound directly to the antigen, radioactive substances, luminescent substances, fluorescent substances, etc., are preferable.

Examples of the method of binding a functional group or marker to the antigen to be assayed to form a modified antigen include the method in which a functional group or marker is directly bound to the antigen via a chemical bond between a reactive group in the antigen and that of the functional group or of the marker.

As for reactive group in the antigen, it is generally —$NH_2$ group in the case of protein hormones. Haptens have a reactive group for binding to protein to form an antibody. Such reactive groups are involved in the chemical bond. Examples of such groups include —$NH_2$ group, —SH group, —COOH group and —CHO group.

When using such a reactive group in the antigen to bind a functional group or a marker to the antigen via a chemical bond, such functional group or marker compound has a reactive group reactive with the reactive group in the antigen. The reactive group reactive to the reactive group in the antigen means a reactive group which reacts with the reactive group in the antigen in a substantially quantitative way. Examples of such reactive groups include N-hydroxysuccinimido group and anhydrides when the antigen has an —$NH_2$ group as the reactive group, and maleimido group and pyridyldisulfido group when the antigen has an —SH group as the reactive group.

Examples of compounds for the introduction of such functional groups include N-sulfosuccinimidyl-6-(biotinamido)hexanoate, 3-(N-maleimido-propionyl)biotin, N-succinimidyl-2,4-dinitrophenyl-5-aminocaproate, $N^6$-biotinyl-L-lysine hydrazide and p-diazobenzoylbiocytin.

Examples of compounds for the introduction of a marker include N-succinimidyl-3-(4-hydroxy-5-[$^{125}$I]iodophenyl)propionate, N-hydroxysuccinimide acridinium ester, europium ($Eu^{3+}$) and chelete compound.

The amount of the compound added to the subject solution for the purpose of introduction of a functional group or marker should be sufficient to ensure efficient reaction of the reactive group in the antigen in the subject solution, since the subject solution contains substances (impurities) having the same reactive group as that in the antigen as well as the antigen to be assayed. Addition of the compound in excess increases the background value, thus reducing the assay sensitivity.

Reaction temperature is normally 0° to 55° C., at which no denaturation occurs in the antigen or the protein in the subject solution, preferably 4° to 40° C. Reaction time is normally 10 minutes to 48 hours, preferably 30 minutes to 12 hours.

It is preferable to add a substance which reacts with the reactive group in the compound to eliminate the reactivity of the unreacted functional group or the compound for introduction of marker after completion of the reaction. Examples of the substance include glycine in the case of N-sulfosuccinimidyl-6(biotinamido)hexanoate and 2-mercaptoethanol in the case of 3-(N-maleimidopropionyl)biotin.

STEP (B or B')

A step to specifically bind the modified antigen to a carrier by means of an antibody against the antigen and in turn separate the modified antigen from the subject solution.

Two methods are available for binding the modified antigen to the carrier via an antibody against the antigen. In the first method [Step (B)], the antibody against the antigen is bound to the carrier and this is followed by reaction with the modified antigen. In the second method [Step (B')], the modified antigen and the antibody against the antigen are reacted together and this is followed by binding to the carrier via the antibody.

In Step (B'), the antibody against the antigen is previously bound with a functional group and this is followed by reaction of the modified antigen and the antibody to form a modified antigen-antibody complex. The functional group (functional group b) used here should not be identical with the functional group (functional group a) used for Step (A). A substance which specifically binds to the functional group is bound to a carrier and this is followed by reaction with the modified antigen-antibody complex.

Examples of substances which specifically bind to the functional group include anti-hapten specific antibodies in the case of hapten and avidin and streptoavidin in the case of biotin.

The antibody against the antigen to be assayed can be obtained by a known method. Accordingly, the antigen or its epitopic site is inoculated to an animal to immunize it to yield a polyclonal or monoclonal antibody. When the antigen or its epitopic site is a hapten, immunization is conducted to obtain the antibody after binding it to protein.

Any carrier can be used, as long as it can serve for immunoassay. Examples of the carrier include polystyrene, polyacryl, Teflon, paper, glass and agarose, etc. There is no particular limitation on their shape.

Examples of the method of binding the antibody against the antigen or the substance which specifically binds to the functional group to the carrier include the method used for the sandwich method to bind an antibody to a carrier.

After binding the modified antigen to the carrier, the carrier is separated from the subject solution.

For this separation, any conventional method used for immunoassay with a carrier can be used.

It is preferable to wash the carrier before proceeding from Step (B) to Step (C) or from Step (B') to Step (C') below.

This washing is achieved under conditions normally used for the sandwich method.

STEP (C) OR FROM STEP (B') TO STEP (C')

This is a step to separate the modified antigen or the modified antigen-antibody complex to be assayed as bound onto the carrier via the antibody against the antigen from the modified impurities bound nonspecifically to the carried.

Dissociation of the modified antigen from the carrier can be achieved by treatment with acid, alkali, concentrated inorganic salt or other substance.

This dissociation is normally achieved at a pH value of below 5, preferably between 0.5 and 3.5 when an acid is used, and at a pH value over 9 when an alkali is used, and at a salt concentration of over 2M when a concentrated inorganic salt is used. This treatment is normally conducted at a temperature of 0° to 45° C. for 10 minutes to scores of hours.

When Step (B') is used, it is possible to dissociate the modified antigen-antibody complex comprising the modified antigen and the antibody against the antigen from the carrier by adding a substance having the same site as that of the functional group bound to the antibody [step (C')].

For example, dinitrophenylamino acid (e.g. dinitrophenyl-lysine) is used when the functional group is dinitrophenyl, and biotin is used when the functional group is biotinyl.

When the functional group is bound to the antibody via the —S—S— bond, the modified antigen-antibody complex can be dissociated using a reagent which breaks the —S—S— bond.

STEP (D) OR (D')

This is a step to assay the modified antigen or modified antigen-antibody complex comprising the modified antigen and the antibody against the antigen, dissociate in step (C'). This step can be conducted by a known method including immunocomplex-transfer method.

To mention an example, in the first method, when the dissociate modified antigen is an antigen bound with a functional group, the modified antigen is assayed by the sandwich method using a carrier bound with a substance which specifically binds with the functional group and marker-bound antibody against the antigen (marker antibody).

Measurement by the sandwich method can be achieved by reaction with the carrier after reaction with the marker antibody, or by reaction with the marker antibody after reaction with the carrier, or by simultaneous reaction of the carrier and the marker antibody.

In the second method, the modified antigen is bound to the carrier via the antibody against the antigen in the same manner as in Step (B) and this is followed by assay noting the functional group or marker in the modified antigen.

When assay is made noting the functional group, the modified antigen is assayed between a marker-labeled substance and a carrier by the sandwich method in which the marker-labeled substance is prepared by marker-labeling a substance which specifically binds with the functional group. Examples of the marker-labeled substance include conjugates of enzyme and avidin or enzyme and streptoavidin.

In methods other than the first method, it is also possible to react the modified antigen bound with the functional group with a marker-labeled substance which specifically binds with the functional group and then carry out reaction for conversion to a marker-labeled modified antigen before Step (D).

The present invention is hereinafter described in more detail by means of the following working examples, but the present invention is not limited to these examples.

EXAMPLE 1

Buffer solution

A 0.01M sodium phosphate buffer solution, pH 7.0, containing 0.1M sodium chloride and 1 g/l bovine serum albumin, was prepared for Solution A.

Preparation of rabbit anti-angiotensin I antiserum

An angiotensin I-bovine serum albumin conjugate was prepared by a known method using glutaraldehyde.

Rabbits were immunized with this angiotensin I-bovine serum albumin conjugate by a known method using Freund's complete adjuvant to yield rabbit anti-angiotensin I antiserum.

Preparation of IgG, F(ab')$_2$, Fab'

IgG, by salting-out with sodium sulfate and using DEAE cellulose, F(ab')$_2$, by pepsine digestion of IgG, and Fab', by reduction of F(ab')$_2$, where each prepared by a known method [Ishikawa et al.: Journal of Immunoassay, 4, 209 (1983)].

Preparation of angiotensin I Sepharose 4B

Angiotensin I (0.5 mg) was insolubilized into activated CH-Sepharose 4B (0.15 g) in accordance with the manual of Pharmacia.

Preparation of affinity purified rabbit anti-angiotensin I Fab'-peroxidase

Rabbit anti-angiotensin I Fab' was labeled with peroxidase by a known method [Hashida et al.: Journal of Applied Biochemistry, 6, 56 (1984)] using N-succinimidyl-6-maleimidohexanoate as a crosslinking agent.

The rabbit anti angiotensin I Fab'-peroxidase was affinity purified by a known method in which elution is conducted at pH 2.5 using an angiotensin I-Sepharose 4B column [K-h. Ruan et al.: Clinical Chimica Acta, 147, 167 (1985)].

Preparation of biotinyl nonspecific rabbit IgG

Biotinyl nonspecific rabbit IgG was prepared by a known reaction between maleimide nonspecific rabbit IgG and N-biotinyl-2-mercaptoethylamine [Kono et al.: Journal of Clinical Laboratory Analysis, 2, 19 (1988)].

Preparation of protein insolubilized solid phase

A rabbit anti-angiotensin I or biotinyl nonspecific rabbit IgG insolubilized polystyrene ball was prepared by physical adsorption onto a polystyrene ball of 3.2 mm in diameter (produced by Precision Plastic Ball Co., Chicago) by a known method [Ishikawa et al.: Scandinavian Journal of Immunology, 8 (Supple. 7), 43 (1978)] using a rabbit anti angiotensin I IgG solution (0.1 g/l) or biotinyl nonspecific rabbit IgG solution (0.1 g/l).

A streptoavidin solution (0.1 g/l) was reacted with the biotinyl nonspecific rabbit IgG insolubilized polystyrene ball at 30° C. for 4 hours to yield a streptoavidin insolubilized polystyrene ball.

Preparation of plasma 7 ml of blood was collected from a normal human into an ice-cooled test tube containing 10.5 mg of disodium ethylene-diamine-tetraacetate (EDTA), and was centrifuged at 4° C. to separate plasma. The plasma was incubated in mixture with an equal volume of a 0.16 mM phosphate buffer solution, pH 4.6, containing 4 mM 8-hydroxyquinoline, an angiotensin I converting enzyme inhibitor, under ice-cooling for 20 minutes, and then 12.5 fold diluted with a 0.1M sodium carbonate buffer solution, pH 9.1, containing 4 mM EDTA.

Preparation of standard solutions 0.56 mg of angiotensin I was dissolved in 0.5 ml of distilled water. This solution was diluted with a 0.1M sodium carbonate buffer solution, pH 8.5, containing 0.16 mM 8-hydroxyquinoline, 4 mM EDTA and 1 g/l bovine serum albumin, to prepare various concentrations of standard solutions.

Assay of angiotensin I

50 μl of the plasma or standard solution was incubated in mixture with 3 μl of dimethylformamide solution containing 88 mM sulfosuccinimidyl-6 (biotinamido)hexanoate at 30° C. for 1 hour and then incubated with 7 μl of 1M glycine-sodium hydroxide, pH 8.5, at 30° C. for 1 hour, and this was followed by the addition of 90 μl of a 10 mM sodium phosphate buffer solution, pH 6.0, containing 1 g/l bovine serum albumin, 0.1M sodium chloride, 1 g/l sodium azide and 4 mM EDTA.

This 150 μl reaction mixture was incubated with the rabbit anti-angiotensin I insolubilized polystyrene ball at 20° C. overnight. After incubation, the reaction mixture was removed, and the polystyrene ball was washed twice with 2 ml of a 10 mM sodium phosphate buffer solution, pH 7.0, containing 0.1M sodium chloride, and this was followed by incubation in the presence of 100 μl of Buffer Solution A and 20 μl of 1M hydrochloric acid at 30° C. for 1 hour.

After polystyrene ball removal, the incubation mixture was neutralized by the addition of 10 μl of a 1M sodium phosphate buffer solution, pH 7.0, and 20 μl of a 0.9M sodium hydroxide. Then, 20 μl of Buffer Solution A containing the affinity purified rabbit anti angiotensin I Fab'-peroxidase (500 fmol), and this was followed by incubation at 20° C. for 3 hours and at 4° C. overnight. Two streptoavidin insolubilized polystyrene balls were then added, and this was followed by incubation at 20° C. for 4 hours while shaking the incubation mixture.

After reaction mixture removal, the polystyrene balls were washed in the same manner as above. The activity of peroxidase bound to the polystyrene balls was then fluorometrically determined at 30° C. over a period of 1 hour by a known method [Imagawa et al.: Analytical Letters, 16 (B19), 1509 (1983)] using 3-(4-hydroxyphenyl)propionic acid as substrate. The intensity of fluorescene was assayed using a 0.2 mg/l quinine solution in 0.05M sulfuric acid as reference substance.

The results of assay on the standard solutions are given in FIG. 1. The detection limit was 13 g (10 amol). When 2 μl of plasma was used, assay was possible up to 6.5 ng/l.

Three different concentrations of angiotensin I (65 to 6400 ng/l) were added to two plasma samples (angiotensin I concentration 56 and 102 ng/l, respectively) and the recoveries of angiotensin I were 85–104%.

The coefficient of variance within assay at 13 different concentrations of samples (56 to 5558 ng/l) was determined to be 1.8–10% (n=5).

The detection limit is lower by over 80 times than the conventional competitive method.

EXAMPLE 2

The same procedures as in Example 1 were followed to prepare a buffer solution, IgG, F(ab')$_2$, Fab', kassinin-Sepharose 4B, affinity purified rabbit anti-kassinin Fab'-peroxidase, biotinyl nonspecific rabbit IgG and protein-insolubilized solid phase.

Preparation of rabbit anti-kassinin antiserum

A kassinin-bovine serum albumin conjugate was prepared by a known method using S-acetylmercapto succinic anhydride and m-maleimidobenzoyl N-hydroxysuccinimide ester.

Rabbits were immunized with the kassinin-bovine serum albumin conjugate by a known method using Freund's complete and incomplete adjuvants to yield rabbit anti-kassinin antiserum.

Preparation of plasma 7 ml of blood was collected from a rat into an ice-cooled test tube containing 10.5 mg of disodium ethylenediaminetetraacetate (EDTA), and was centrifuged at 4° C. to separate plasma. This blood plasma was 25 fold diluted with a 0.1M sodium phosphate buffer solution, pH 7.5, containing 4 mM EDTA before assay.

Preparation of standard solutions 1.0 mg of kassinin was dissolved in 0.5 ml of distilled water. This solution was diluted with a 0.1M sodium phosphate buffer solution, pH 7.5, containing 4 mM EDTA and 1 g/l bovine serum albumin to yield various concentrations of standard solutions.

Assay of kassinin

50 μl of the plasma or standard solution was incubated in mixture with 3 μl of dimethylformamide solution containing 53 mM sulfosuccinimidyl-6-(biotinamido)hexanoate at 30° C. for 1 hour and then incubated with 7 μl of 1M glycine-sodium hydroxide, pH 8.0, at 30° C. for 1 hour, and this was followed by the addition of 90 μl of a 10 mM sodium phosphate buffer solution, pH 6.0, containing 1 g/l bovine serum albumin, 0.1M sodium chloride, 1 g/l sodium azide and 4 mM EDTA.

This 150 μl reaction mixture was incubated with the rabbit anti-kassinin insolubilized polystyrene ball at 20° C. overnight. After incubation, the reaction mixture was removed, and the polystyrene ball was washed twice with 2 ml of a 10 mM sodium phosphate buffer solution, pH 7.0, containing 0.1M sodium chloride, and this was followed by incubation in the presence of 100 μl of Buffer Solution A and 20 μl of hydrochloric acid at 30° C. for 1 hour.

After polystyrene ball removal, the incubation mixture was neutralized by the addition of 10 μl of a 1M sodium phosphate buffer solution, pH 7.0, and 20 μl of 0.9M sodium hydroxide. Then, 20 μl of Buffer Solution A containing the affinity purified rabbit anti-kassinin Fab'-peroxidase (50 fmol) was added, and this was followed by incubation at 20° C. for 3 hours and at 4° C. overnight. Two streptoavidin insolubilized polystyrene balls were then added, and this was followed by incubation at 20° C. for 4 hours while shaking the incubation mixture.

After reaction mixture removal, the polystyrene balls were washed in the same manner as above. The activity of peroxidase bound to the polystyrene balls was then fluorometrically determined at 30° C. over a period of 1 hour by a known method [Imagawa et al.: Analytical Letters, 16 (B19), 1509 (1983)] using 3-(4-hydroxyphenyl)propionic acid as substrate. The intensity of fluorescenece was assayed using a 0.2 mg/l quinine solution in 0.05M sulfuric acid as reference substance.

Figure 2:
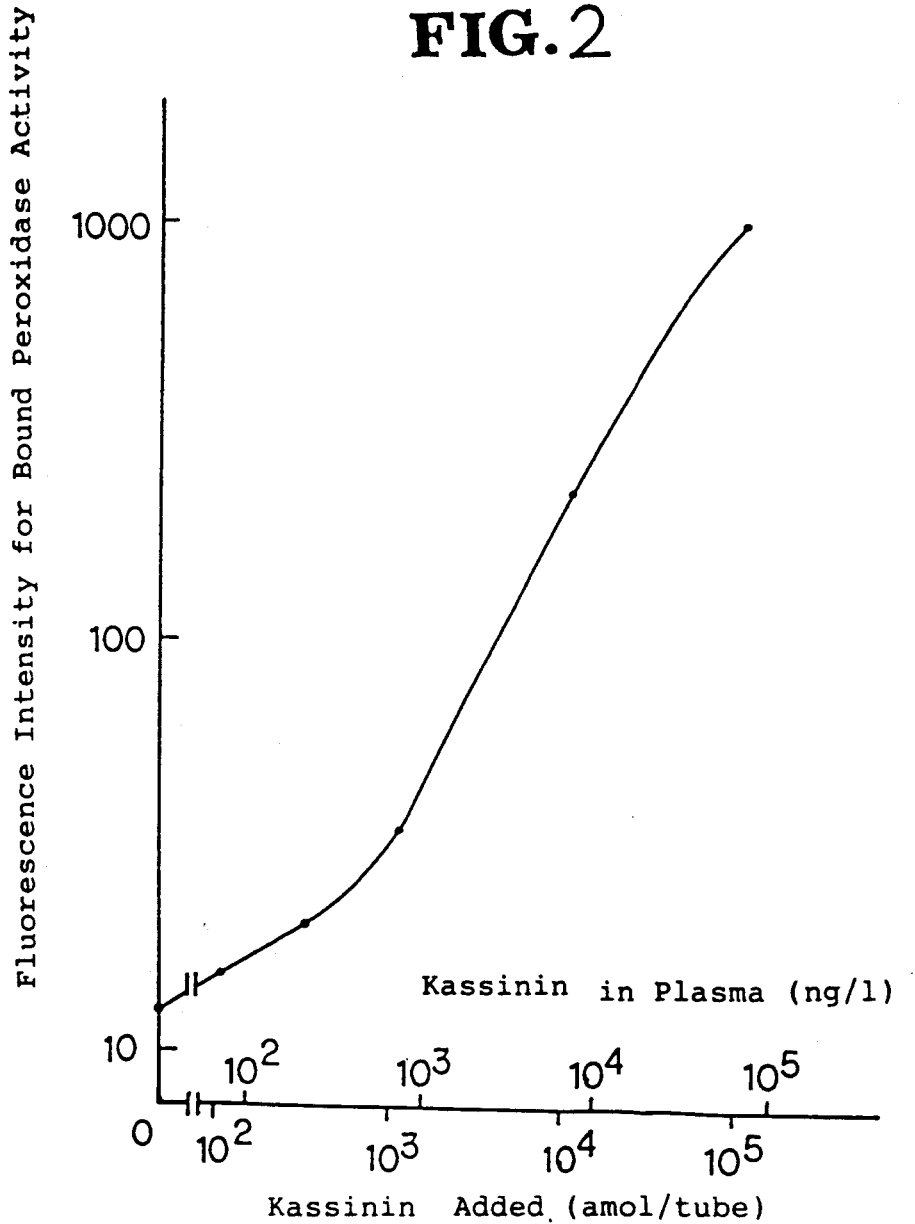

The results of assay on the standard solutions are given in FIG. 2. The detection limit was 130 fg (100 amol). When 2 μl of plasma was used, assay was possible up to 65 ng/l.

Three different concentrations of kassinin (650 to 19500 ng/l) were added to plasma; the recoveries of kassinin were 101–119%. The coefficient within assay at six different concentrations of samples (840 to 26700 ng/l) was 7.9–13% (n=5).

COMPARATIVE EXAMPLE 1

Buffer solution

A 0.05M sodium phosphate buffer solution, pH 7.0, containing 0.15M sodium chloride, 0.1% gelatin and 0.02% sodium azide, was prepared for Buffer Solution B.

Rabbit anti-kassinin antiserum

The same antiserum as in Example 2 was used.

Preparation of $^{125}$I-tyrosinated kassinin

N-terminal tyrosinated kassinin was labeled by a known method using Na$^{125}$I and chloramine T to yield $^{125}$I-tyrosinated kassinin.

The specific radioactivity of the $^{125}$I-tyrosinated kassinin was 11 μCi/μg.

Preparation of standard solutions 0.5 mg of kassinin was dissolved in 1 ml of a 0.1M borate buffer solution, pH 8.5, and this solution was diluted with Buffer Solution B to yield various concentrations of standard solutions.

Radioimmunoassay for kassinin

100 μl of each standard solution was incubated with 200 μl of a rabbit anti-kassinin antiserum solutions as 1000 fold diluted with Buffer Solution B, 100 μl (10000 cpm) of $^{125}$I-tyrosinated kassinin solution in Buffer Solution B and 200 μl of Buffer Solution B at 4° C. for 18 hours.

Then, 200 μl of a suspension in Buffer Solution B containing 0.25% dextran T-70 and 2.5% activated charcoal (Norit A) was added. The resulting mixture was kept standing at 4° C. for 15 minutes and then centrifuged at 3000 rpm for 20 minutes. The radioactivity of the supernatant was determined using a γ-counter.

Figure 3:
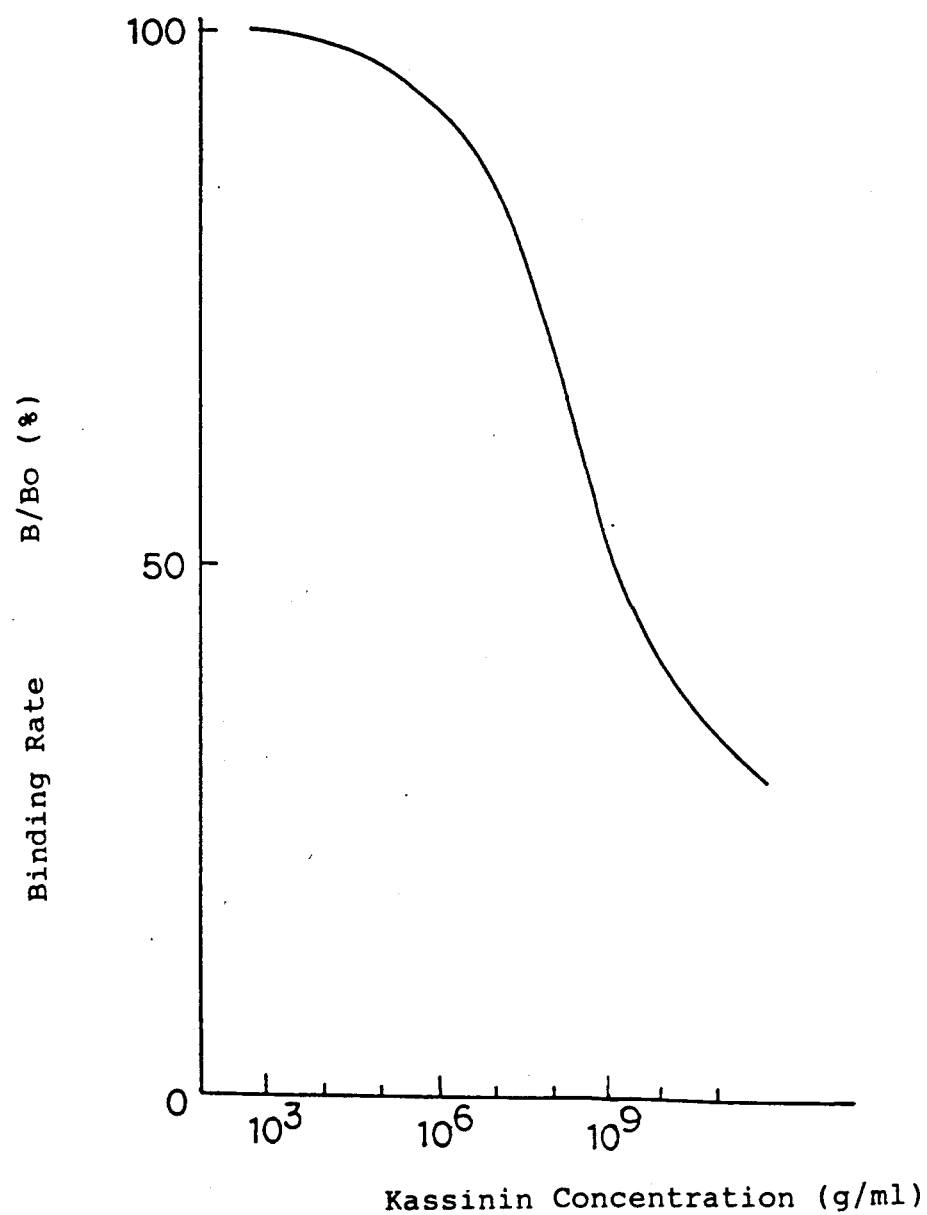
FIG. 3 shows the standard curve of assay for antigen by the conventional method as obtained in Comparative Example.

The results of assay on the standard solutions are given in FIG. 3. The detection limit was 100 pg (75 fmol).

The detection limit obtained by the present invention as in Example 2 is lower by 750 times than that obtained by the conventional competitive method as in Comparative Example 1.

EXAMPLE 3

Buffers

The regularly used buffers were 10 mmol/l sodium phosphate buffer, pH 7.0, containing 0.1 mol/l NaCl and 1 g/l bovine serum albumin (crystallized, Miles Laboratories, Ltd., Elkhart, Ind. USA) (buffer A), and 0.1 mol/l sodium phosphate buffer, pH 7.0, containing 0.1 mol/l NaCl, 1 g/l bovine serum albumin and 1 mmol/l ethylenediaminetetraacetate (EDTA)(buffer C).

Preparation of rabbit anti-arginine vasopressin antibody

Anti-arginine vasopressin serum was raised in male New Zealand white rabbits by eight intracutaneous injections of arginine vasopressin-bovine thyroglobulin conjugate at 2-3 week intervals.

Arginine vasopressin (5 mg, Peptide Institute, Inc., Osaka, Japan) was conjugated to bovine thyroglobulin (50 mg, Sigma Chemical Company, St. Louis, Mo., USA) by the carbodiimide method [Journal of Laboratory and Clinical Medicine, 80 134–144 (1972)] using 1-ethyl-3-(3-dimethylaminopropyl)carbodiimide (Calbiochem-Behring, La Jolla, Calif., USA). For injection, the conjugate in saline (0.4 mg/ml) was emulsified with an equal volume of Freund's complete adjuvant (Miles Laboratories, Inc.). The amount of the conjugate injected was 0.2 mg per rabbit. Blood was collected 13 days after the last immunization, and the antiserum was stored at −20° C.

IgG, F(ab')$_2$ and Fab' were prepared in accordance with the method of Example 1. The amount of IgG and its fragments was calculated from the absorbance at 280 nm.

Arginine Vasopressin-Sepharose 4B

Arginine vasopressin (0.61 mg) was coupled to activated CH-Sepharose 4B (0.17 g, Pharmacia Fine Chemicals AB, Uppsala, Sweden) according to the instructions of Pharmacia.

Affinity-Purified Anti-Arginine Vasopressin Fab'-Peroxidase Conjugate

Anti-arginine vasopressin Fab' was conjugated to horseradish peroxidase (Grade I, Re (Grade I, RZ=3.0, Boehringer Mannheim GmbH, Mannheim, FRG) using N-succinimidyl-6-maleimidohexanoate (Dojindo Laboratories, Kumamoto, Japan) by a known method [Hashida et al., Journal of applied biochemistry (mentioned above)].

The conjugate was affinity-purified by elution from a column of arginine vasopressin-Sepharose 4B at pH 2.5 in accordance with a known method [Ruan et al., Clinica Chimica Acta, 147, 167–172 (1985)].

Protein-Coated Polystyrene Balls

Polystyrene balls (3.2 mm in diameter, Immunochemical Co., Okayama, Japan) were coated with rabbit anti-arginine vasopressin IgG (0.1 g/l) in accordance with the method of Example 1. Biotinyl nonspecific rabbit IgG, biotinyl nonspecific rabbit IgG-coated polystyrene balls and Streptavidin-coated polystyrene balls were prepared as mentioned in Example 1. The protein-coated polystyrene balls were stored in buffer A containing 1 g/l NaN$_3$ at 4° C.

Dilution of Urine Samples and Arginine Vasopressin

Urine samples were obtained as first morning voids from healthy subjects aged 22-35 yr and were diluted 20-fold with buffer C.

Arginine vasopressin (0.61 mg) was dissolved in 0.5 ml of 0.2 mol/l acetic acid and diluted with buffer C.

Assay of arginine vasopressin

Biotinylation was performed in two different ways.
① Direct biotinylation.—A 100 μl aliquot of the diluted arginine vasopressin or the diluted urine was incubated with 10 μl of 66 mmol/l N-hydroxysuccinimidobiotin (Zymed Laboratories, Inc., San Francisco, Calif., USA) in dimethylsulfoxide at 20° C. for 1 hour. After incubation, the reaction mixture was incubated with 10 μl of 1 mol/l glycine-NaOH, pH 7.0, at 20° C. for 30 minutes, followed by addition of 30 μl of buffer C containing 5 g/l NaN₃.

②  Indirect Biotinylation.—A 100 μl aliquot of the diluted arginine vasopressin or the diluted urine was incubated with 5 μl of 63 mmol/l N-succinimidyl-6-maleimidohexanoate (Dojindo Lab.) in dimethylsulfoxide at 20° C. for 1 hour. After incubation, the reaction mixture was incubated with 5 μl of 99 mmol/l glutathione (reduced form, Dojindo Lab.) in 0.1 mol/l sodium phosphate buffer, pH 7.0, containing 1 mmol/l EDTA at 20° C. for 1 hour and subsequently with 5 μl of 138 mmol/l N-hydroxysuccinimidobiotin (Zymed Lab., Inc.) in dimethylsulfoxide at 20° C. for 1 hour. Finally, 5 μl of 2 mol/l glycine-NaOH, pH 7.0, was added, and the incubation was continued at 20° C. for 30 minutes, followed by addition of 30 μl of buffer C containing 5 g/l NaN₃. The above procedures are summarized in the following diagram.

EDTA and 20 μl of 1 mol/l HCl at 4° C. for 1 hour. After removal of the polystyrene balls, the remaining solution was neutralized by addition of the mixture of 10 μl of 1 mol/l sodium phosphate buffer, pH 7.0, and 20 μl of 1 mol/l NaOH. The neutralized mixture was incubated with affinity-purified anti-arginine vasopressin Fab'-peroxidase conjugate (200 fmol) and nonspecific rabbit F(ab')₂ (0.1 mg) in 20 μl of buffer A at 4° C. overnight. Subsequently, two streptavidin-coated polystyrene balls were added, and the incubation was continued at 4° C. for 5 hours. After removal of the reaction mixture, the polystyrene balls were washed twice as described above, and peroxidase activity bound to the polystyrene balls was assayed at 30° C. for 60 minutes using 3-(4-hydroxyphenyl)propionic acid as substrate in accordance with the method of Example 1. Fluorescence intensity was assayed relative to 0.2 mg/l quinine in 50 mmol/l H₂SO₄ using 320 nm for excitation and 405 nm for emission with a Shimadzu fluorophotometer (RF-510, Shimadzu Seisakusho, Ltd., Kyoto, Japan).

The detection limit of arginine vasopressin was taken as the minimal amount of arginine vasopressin which gave a bound peroxidase activity significantly in excess

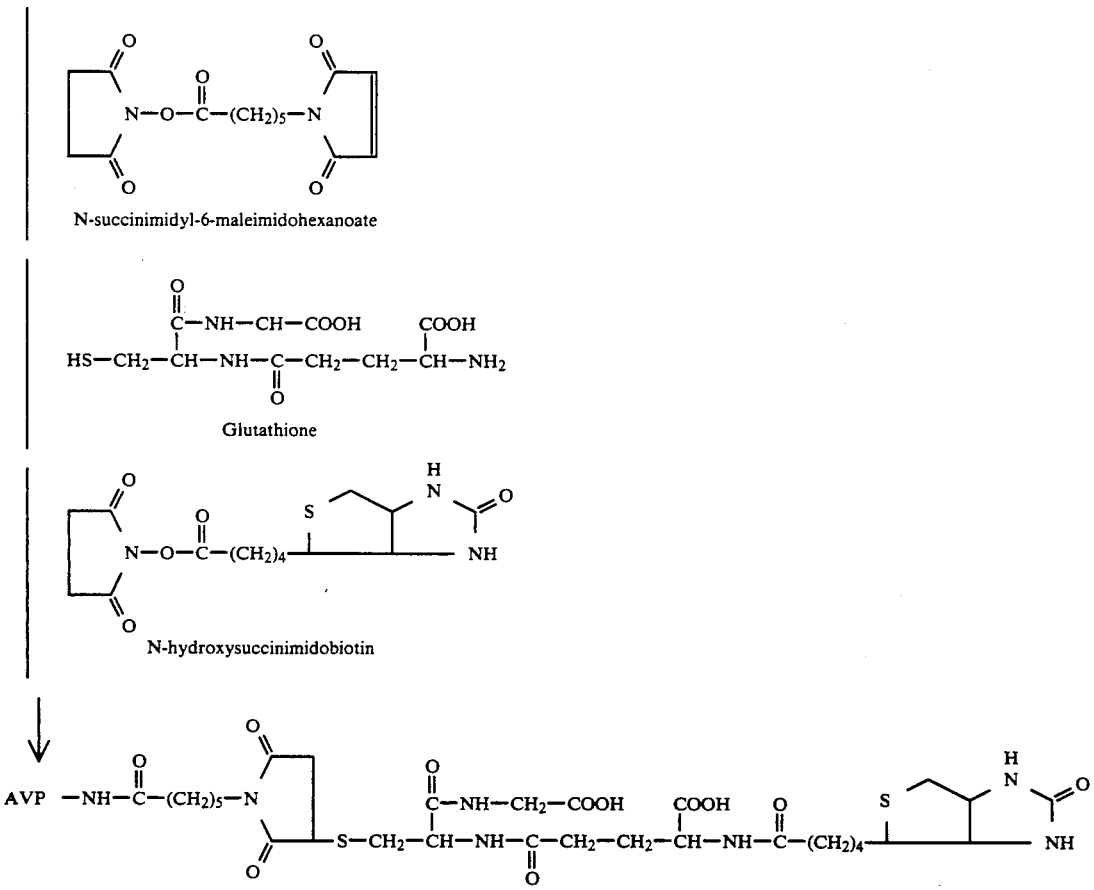

The biotinylated mixture (150 μl) was incubated with two anti-arginine vasopressin IgG-coated polystyrene balls at 4° C. overnight. After incubation, the polystyrene balls were washed twice by addition and aspiration of 2 ml of 10 mmol/l sodium phosphate buffer, pH 7.0, containing 0.1 mol/l NaCl, and were incubated with the mixture of 100 μl of buffer A containing 1 mmol/l of that nonspecifically bound in the absence of arginine vasopressin (background). The existence of a significant difference from the background was confirmed by the t-test (p<0.001, n=5).

Figure 4:
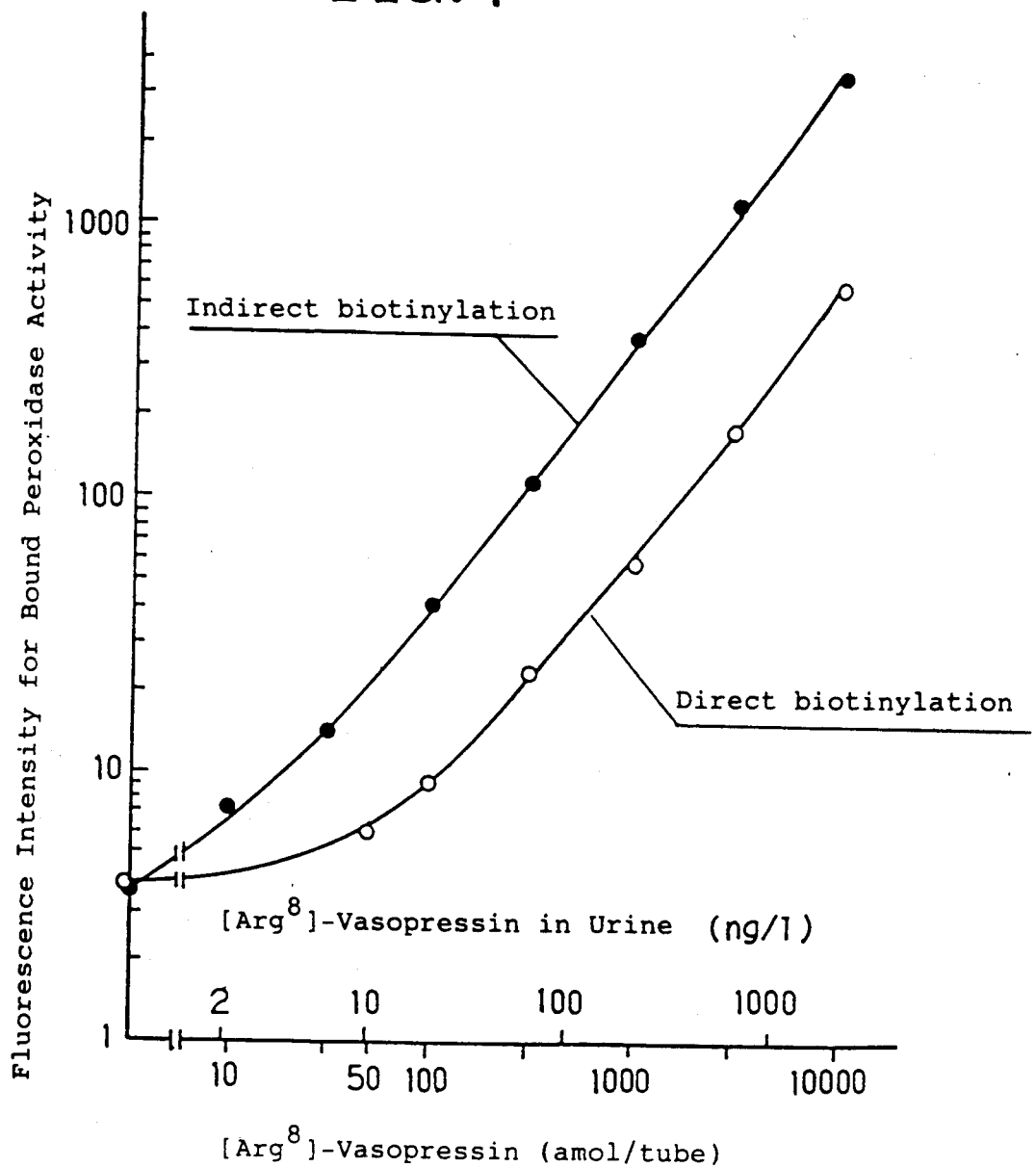

① In the case of direct biotinylation, the detection limit of arginine vasopressin was 54 fg (50 amol)/tube (FIG. 4, open circle).

② In the case of indirect biotinylation, the detection limit of arginine vasopressin by indirect biotinylation was 11 fg (10 amol)/tube (FIG. 4, closed circle). This was 23 to 400-fold lower than those previously reported by competitive radioimmunoassay [Morton et al., Journal of Endo-crinology, 65 411–424 (1975)][Granzer et al., Acta Endocrinologica, 106 317–329 (1984)] and competitive enzyme immunoassay [Uno et al., Experimentia 38 786–787 (1982)]. The assay range of arginine vasopressin in urine was 2–2,000 ng/l using 5 μl of samples.

The recoveries of arginine vasopressin added to urine samples were 86.4±7.6 (SD % (range, 77–101%; n=18), when arginine vasopressin at two different levels (20 and 80 ng/l) was added to 9 urine samples (5 μl) containing 6.6–63.5 ng/l of arginine vasopressin. The assay precision was examined at 14 different arginine vasopressin levels over the range of 6.6–117.3 ng/l prepared with and without addition of arginine vasopressin to urine samples. The coefficient of within-assay variation was 3.0–12.6% (n=5).

Indirect biotinylation technique, which could delete the possibility of steric hindrance caused by biotin residues bound fairly close to the epitopic sites of arginine vasopressin could lower the detection limit of the peptide 5 fold than that of direct biotinylation. This suggested that haptens with amino groups could also be assayed with high sensitivity in a similar manner.

As stated above, the present invention permits assay for antigens with high sensitivity based on characteristic features of the sandwich method, using an antibody against a single epitopic site, and also permits assay for low molecular substances, which have never been assayed by the conventional sandwich method, with much higher sensitivity than that of the conventional competitive method, as does the sandwich method.

What is claimed is:

1. A method of assaying an antigen with one epitopic site and comprising the following sequential steps (A), (B), (C), and (D):
    (A): Binding the antigen to be assayed in a subject solution with a hapten or biotinyl group, which specifically binds with a substance used for sandwich methods in (D) to form a modified antigen;
    (B): Binding the modified antigen to a carrier via an antibody against the antigen and then separating the carrier from the subject solution;
    (C): Either (a) or (b):
        (a) Dissociating the modified antigen from the carrier;
        (b) Dissociating the modified antigen-antibody complex, comprising the modified antigen and the antibody against the antigen, from the carrier; and
    (D): Assaying the modified antigen or modified antigen-antibody complex of (C) by sandwich method.

2. The method of claim 1 wherein the antigen is a hapten.

3. A method as claimed in claim 1 wherein the antigen is a hapten having an —$NH_2$ group as a reactive group or an antigen with one epitope having an —$NH_2$ group as a reactive group.

4. A method as claimed in claim 1 wherein the hapten is a dinitrophenyl group, a trinitrophenyl group or a fluorescein group.

5. A method of assay for antigen with one epitopic site comprising the following sequential steps (A), (B), (C), and (D):
    (A): binding the antigen to be assayed in a subject solution with a hapten or biotinyl group, which specifically binds with a substance used for sandwich methods in (D), to form a modified antigen,
    (B): binding the modified antigen to a carrier via an antibody against the antigen and then separating the carrier from the subject solution,
    (C) dissociating the modified antigen from the carrier, and
    (D): assaying the modified antigen of step (C) by sandwich method.

6. A method of assay for antigen with one epitopic site comprising the following sequential steps (A), (B'), (C'), and (D):
    (A): binding the antigen to be assayed in a subject solution with a hapten or biotinyl group, which specifically binds with a substance used for sandwich methods in (D), to form a modified antigen,
    (B'): binding an antibody against the antigen with a hapten or biotinyl group other than the hapten or biotinyl group used in step (A), reacting the antibody with the modified antigen to form a modified antigen-antibody complex, binding the complex to carrier via a substance which specifically binds to the hapten or biotinyl group, other than the hapten or biotinyl group used in (A), and then separating the carrier from the subject solution,
    (C'): dissociating the modified antigen-antibody complex from the carrier by adding thereto a substance having the same binding site as that of the hapten or biotinyl group bound to the antibody in step (B'), and
    (D): assaying the modified antigen-antibody complex of (C') by sandwich method.

7. A method as claimed in claim 4 wherein the hapten is a dinitrophenyl group.

* * * * *